(12) United States Patent
Grass et al.

(10) Patent No.: US 11,918,291 B2
(45) Date of Patent: Mar. 5, 2024

(54) SIMULATION OF TRANSCATHETER AORTIC VALVE IMPLANTATION (TAVI) INDUCED EFFECTS ON CORONARY FLOW AND PRESSURE

(71) Applicant: KONINKLIJKE PHILIPS N.V., Eindhoven (NL)

(72) Inventors: Michael Grass, Buchholz in der Nordheide (DE); Sven Prevrhal, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 691 days.

(21) Appl. No.: 16/499,338

(22) PCT Filed: Apr. 1, 2018

(86) PCT No.: PCT/EP2018/058373
§ 371 (c)(1),
(2) Date: Sep. 30, 2019

(87) PCT Pub. No.: WO2018/178381
PCT Pub. Date: Oct. 4, 2018

(65) Prior Publication Data
US 2021/0093382 A1  Apr. 1, 2021

Related U.S. Application Data

(60) Provisional application No. 62/557,205, filed on Sep. 12, 2017, provisional application No. 62/479,634, filed on Mar. 31, 2017.

(51) Int. Cl.
*A61B 34/10* (2016.01)
*G16H 20/40* (2018.01)
(Continued)

(52) U.S. Cl.
CPC .............. *A61B 34/10* (2016.02); *G16H 20/40* (2018.01); *G16H 50/50* (2018.01); *A61B 6/507* (2013.01);
(Continued)

(58) Field of Classification Search
CPC ... G16H 20/40; G16H 50/50; A61B 2034/104
(Continued)

(56) References Cited

U.S. PATENT DOCUMENTS 9,141,763 B2   9/2015 Sharma
9,855,105 B2 * 1/2018 Taylor ..................... A61B 5/22
(Continued)

FOREIGN PATENT DOCUMENTS

EP         3422226 A1    1/2019
WO    WO2016002054 A1   1/2016
(Continued)

OTHER PUBLICATIONS

"Model analysis of Red Blood Cell flow through diverging and converging Microvascular bifurcations" Javid Amini, the school of engineering and applied science of the George Washington university, May 1994.*
(Continued)

*Primary Examiner* — Javid A Amini
(74) *Attorney, Agent, or Firm* — Larry Liberchuk

(57) ABSTRACT

A computing system (118) includes a computer readable storage medium (122) with computer executable instructions (124), including: a biophysical simulator (126) configured to simulate coronary or carotid flow and pressure effects induced by a cardiac valve device implantation, using cardiac image data and a device model (212). The computing system further includes a processor (120) configured to execute the biophysical simulator to simulate the coronary or carotid flow and the pressure effects induced by the device
(Continued)

implantation with the cardiac image data and the device model. The computing system further includes a display configured to display results of the simulation.

15 Claims, 6 Drawing Sheets

(51) Int. Cl.
*G16H 50/50* (2018.01)
*A61F 2/24* (2006.01)

(52) U.S. Cl.
CPC ....... *A61B 2034/104* (2016.02); *A61F 2/2427* (2013.01)

(58) Field of Classification Search
USPC ...................................................... 703/9, 11
See application file for complete search history.

(56) References Cited

U.S. PATENT DOCUMENTS

| | | | |
|---|---|---|---|
| 10,373,700 B2 | 8/2019 | Sharma | |
| 10,682,180 B2* | 6/2020 | Taylor | G06T 7/73 |
| 2011/0153286 A1 | 6/2011 | Zaeuner | |
| 2012/0053921 A1* | 3/2012 | Taylor | A61B 6/03 703/11 |
| 2014/0058715 A1 | 2/2014 | Sharma | |
| 2014/0336995 A1 | 11/2014 | Singer | |
| 2015/0348260 A1* | 12/2015 | Sharma | G06F 18/214 382/128 |
| 2015/0370995 A1* | 12/2015 | Wakai | G06F 17/16 703/2 |
| 2016/0128786 A1 | 5/2016 | Weber | |
| 2016/0303804 A1 | 10/2016 | Brbic | |
| 2017/0076637 A1 | 3/2017 | Kheradvar | |
| 2017/0109496 A1* | 4/2017 | Hisada | G16H 50/50 |
| 2019/0298450 A1* | 10/2019 | Dasi | A61B 6/03 |
| 2021/0118569 A1* | 4/2021 | Grass | A61B 6/503 |
| 2021/0196391 A1* | 7/2021 | Taylor | A61B 8/065 |
| 2022/0084684 A1* | 3/2022 | Giddens | A61B 5/026 |

FOREIGN PATENT DOCUMENTS

| | | |
|---|---|---|
| WO | WO2016087396 A1 | 6/2016 |
| WO | WO2017083401 A1 | 5/2017 |
| WO | WO2018097902 A1 | 5/2018 |
| WO | WO2018108276 A1 | 6/2018 |
| WO | WO2018185298 A1 | 10/2018 |

OTHER PUBLICATIONS

PCT International Search Report, International application No. PCT/EP2018/058373, dated Aug. 3, 2018.
Ecabert O. et al., "Automatic Model-Based Segmentation of the Heart in CT Images." IEEE Transactions on Medical Imaging, vol. 27, No. 9, Sep. 2008, pp. 1189-1201.
Nickisch et al., "Learning Patient-Specific Lumped Models for Interactive Coronary Blood Flow Simulations," in Medical Image Computing and Computer-Assisted Intervention—MICCAI 2015: 18th International Conference, LNCS, vol. 9350, 2015, pp. 433-441.
Bosmans B. et al., "A Validated Methodology for Patient Specific Computational Modeling of Self-Expandable Transcatheter Aortic Valve Implantation", Journal of Biomechanics, vol. 49, (2016), pp. 2824-2830.
Capelli C. et al., "Patient-Specific Simulations of Transcatheter Aortic Valve Stent Implantation", Medical & Biological Engineering & Computing, Feb. 2012, vol. 50, pp. 183-192.
De Tullio M D et al., "On the Effect of Aortic Root Geometry on the Coronary Entry-Flow After a Bileaflet Mechanical Heart Valve Implant: A Numerical Study", Acta Mechanica, Springer-Verlag, vol. 216, No. 1-4, Jul. 6, 2010, pp. 147-163, XP019856224.

* cited by examiner

SIMULATION OF TRANSCATHETER AORTIC VALVE IMPLANTATION (TAVI) INDUCED EFFECTS ON CORONARY FLOW AND PRESSURE

FIELD OF THE INVENTION

The following generally relates to an approach for the simulation of coronary flow and pressure effects induced by transcatheter aortic valve implantation (TAVI), and is described with particular application to computed tomography, and is also amenable to X-ray, magnetic resonance imaging, and/or other imaging modalities.

BACKGROUND OF THE INVENTION

Transcatheter aortic valve implantation (TAVI) is a minimally invasive procedure to replace an aortic valve of the heart through the blood vessels, e.g., for a valve that fails to open properly due to aortic valve stenosis. The valve has been inserted through one of the following: transfemoral (in the upper leg), transapical (through the wall of the heart), subclavian (beneath the collar bone), direct aortic (through a minimally invasive surgical incision into the aorta), and transcaval (from a temporary hole in the aorta near the belly button through a vein in the upper leg).

Unfortunately, the implantation can cause a flow and/or pressure change distal to the valve in the aorta and hence the coronary and/or carotid arteries. With respect to the coronary arteries, this can change a flow relevance of a stenosis in coronary arteries. For example, a fractional flow reserve measurement or simulation (which is a ratio of a pressure distal to a stenosis to a pressure proximal to the stenosis) may be less than 0.8 after an implantation, where it was 0.8 or greater before the implantation. Where the established clinical threshold for functional significance is 0.8, this could lead to a change in patient care after the valve implantation, e.g., a stent implantation and/or other treatment.

SUMMARY OF THE INVENTION

Aspects described herein address the above-referenced problems and others.

In one aspect, a computing system includes a computer readable storage medium with computer executable instructions, including: a biophysical simulator configured to simulate coronary or carotid flow and pressure effects induced by a cardiac valve device implantation, using cardiac image data and a device model. The computing system further includes a processor configured to execute the biophysical simulator to simulate the coronary or carotid flow and the pressure effects induced by the device implantation with the cardiac image data and the device model. The computing system further includes a display configured to display results of the simulation.

In another aspect, a computer readable storage medium is encoded with computer readable instructions, which, when executed by a processor of a computing system, causes the processor to: receive cardiac image data, obtain a device model of a cardiac valve device implant, simulate coronary or carotid flow and the pressure effects induced by the device implant with the cardiac image data and the device model, and display results of the simulation.

In another aspect, a method includes receiving cardiac image data and receiving a device model of a cardiac valve device implant. The method further includes simulating coronary or carotid flow and the pressure effects induced by the device implant with the cardiac image data and the device model. The method further includes visually displaying results of the simulation.

Those skilled in the art will recognize still other aspects of the present application upon reading and understanding the attached description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
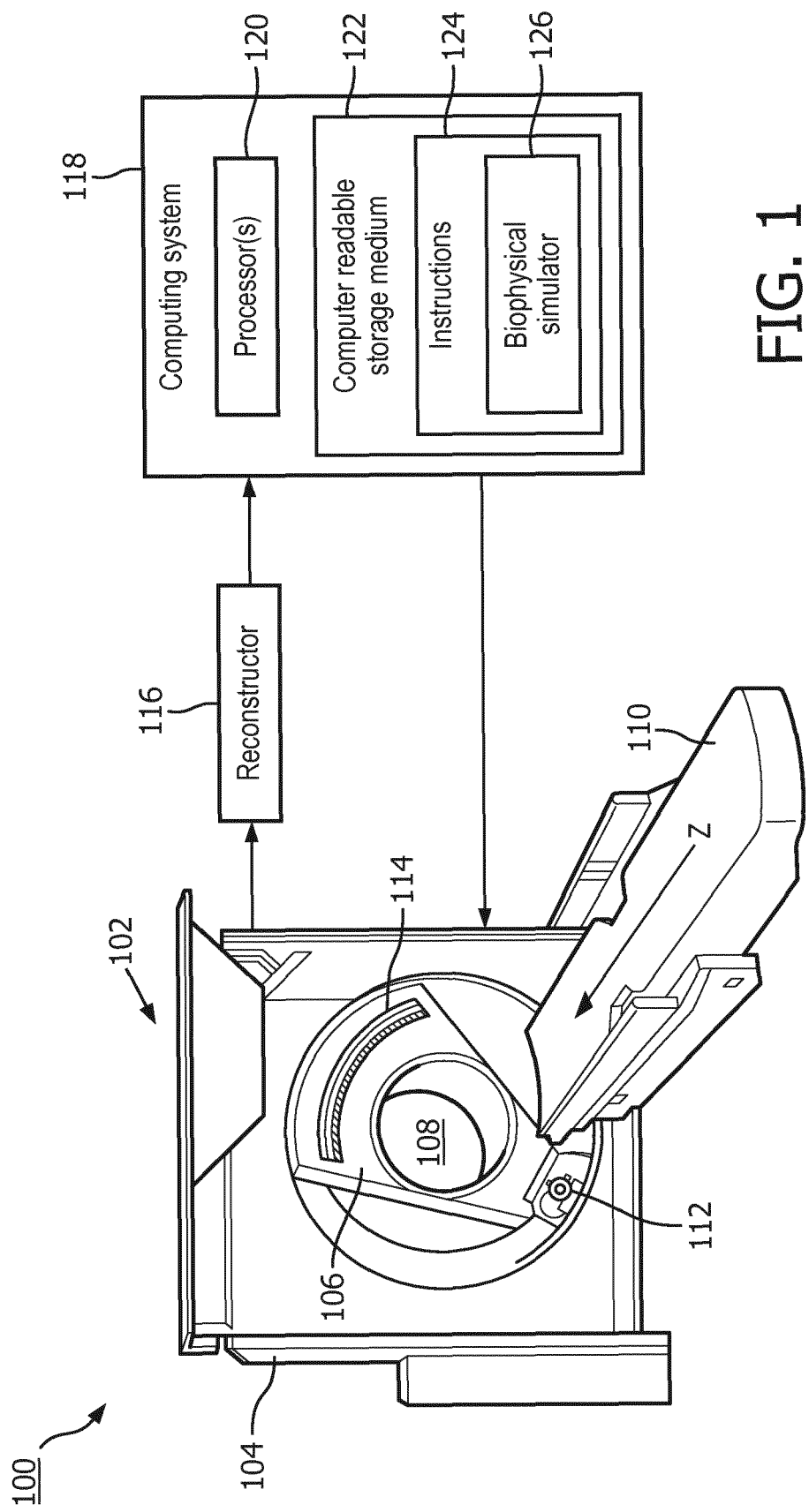
FIG. 1 schematically illustrates a system, including a computing system, with a biophysical simulator, and an imaging system.

FIG. 1 schematically illustrates a system 100 including an imaging system 102 such as a CT scanner. In a variation, the system 100 includes a magnetic resonance (MR), X-ray, and/or other imaging modality. The illustrated imaging system 102 includes a generally stationary gantry 104 and a rotating gantry 106, which is rotatably supported by the stationary gantry 104 and rotates around an examination region 108 about a z-axis. A subject support 110, such as a couch, supports an object or subject in the examination region 108.

A radiation source 112, such as an x-ray tube, is rotatably supported by the rotating gantry 106, rotates with the rotating gantry 106, and emits radiation that traverses the examination region 108. A radiation sensitive detector array 114 subtends an angular arc opposite the radiation source 112 across the examination region 108. The array 114 detects radiation traversing the examination region 108 and generates an electrical signal(s) (projection data) indicative thereof.

A reconstructor 116 reconstructs the projection data, generating volumetric image data indicative of the examination region 108. In one instance, the volumetric image data includes a coronary computed tomography angiogram (CCTA), which is acquired during a contrast enhanced coronary computed tomography angiography of the heart of a patient. The CCTA image data can be a 3-D single phase data set or a 4-D multiple phase data set over multiple cardiac phases of the heart.

The system 100 further includes a computing system 118, which, in this example, serves as an operator console. The console 118 includes a processor 120 (e.g., a microprocessor, a central processing unit, etc.) and a computer readable storage medium 122, which excludes transitory medium, and includes non-transitory medium such as a physical memory device, etc. The console 118 further includes a human readable output device(s) such as a display monitor, and an input device(s) such as a keyboard, mouse, etc.

The computer readable storage medium 122 includes instructions 124 for a biophysical simulator 126. The processor 120 is configured to execute the instructions 124 and/or software that allows the operator to interact with and/or operate the scanner 102 via a graphical user interface (GUI) or otherwise. The processor 120 may additionally, or alternatively, execute a computer readable instruction(s) carried by a carrier wave, a signal and/or other transitory medium.

In a variation, the biophysical simulator 126 is part of another computing system, which is separate from the console 118 and the system 100. In this instance, the other computing system is similar to the console 118 in that it includes a processor, computer readable storage medium, an input device, and an output device, but it does not include the software that allows the operator to interact with and/or operate the scanner 102. The other computing system can be a dedicated computing system (e.g., a computer workstation, etc.) and/or part of shared computer processing resources such a "cloud" based computing.

The biophysical simulator 126 is configured to process the image data (e.g., CT, X-ray, MR) and perform a biophysical simulation. As described in greater detail below, in one instance this includes segmenting certain cardiac anatomy (e.g., aortic, mitral, tricuspid, and/or pulmonary valves, coronary arteries, right and/or left atriums, right and/or ventricles, pulmonary artery, and/or aorta, etc.) from the image data, "virtually" implanting a digital (aortic, mitral, tricuspid, and/or pulmonary) valve model into the segmented image data ("virtual valve implantation"), simulating a pressure and/or flow after the valve with and without the implantation, and predicting an index such as a fractional flow reserve (FFR), an instantaneous wave-free ratio (iFR), Coronary Flow Reserve (CFR) and/or other index. In one instance, this provides comprehensive simulation of the valve and artery function prior and post valve implantation.

The biophysical simulator 126 can be based on physical modelling, (supervised, partially supervised or unsupervised) machine learning/deep learning (e.g., neural networks), etc. The simulation can be performed based on 2-D (e.g., one or more images), 3-D and/or 4-D data sets. With 4-D data, a multi-phase simulation can be carried out and functional parameters such as wall motion, ejection fraction, etc. can be included into the simulation. Although the approach described herein can simulate and predict the influence of implantation of any of the valves on flow and/or pressure, the below, for sake of brevity and explanatory purposes, describes simulating and predicting the influence of a TAVI on the functional performance of the coronary arteries in detail. Generally, the change in flow boundary conditions into the coronaries may change cardiac phase dependent. The changing boundary conditions for flow into the carotid arteries can also be a target of the simulation.

Figure 2:
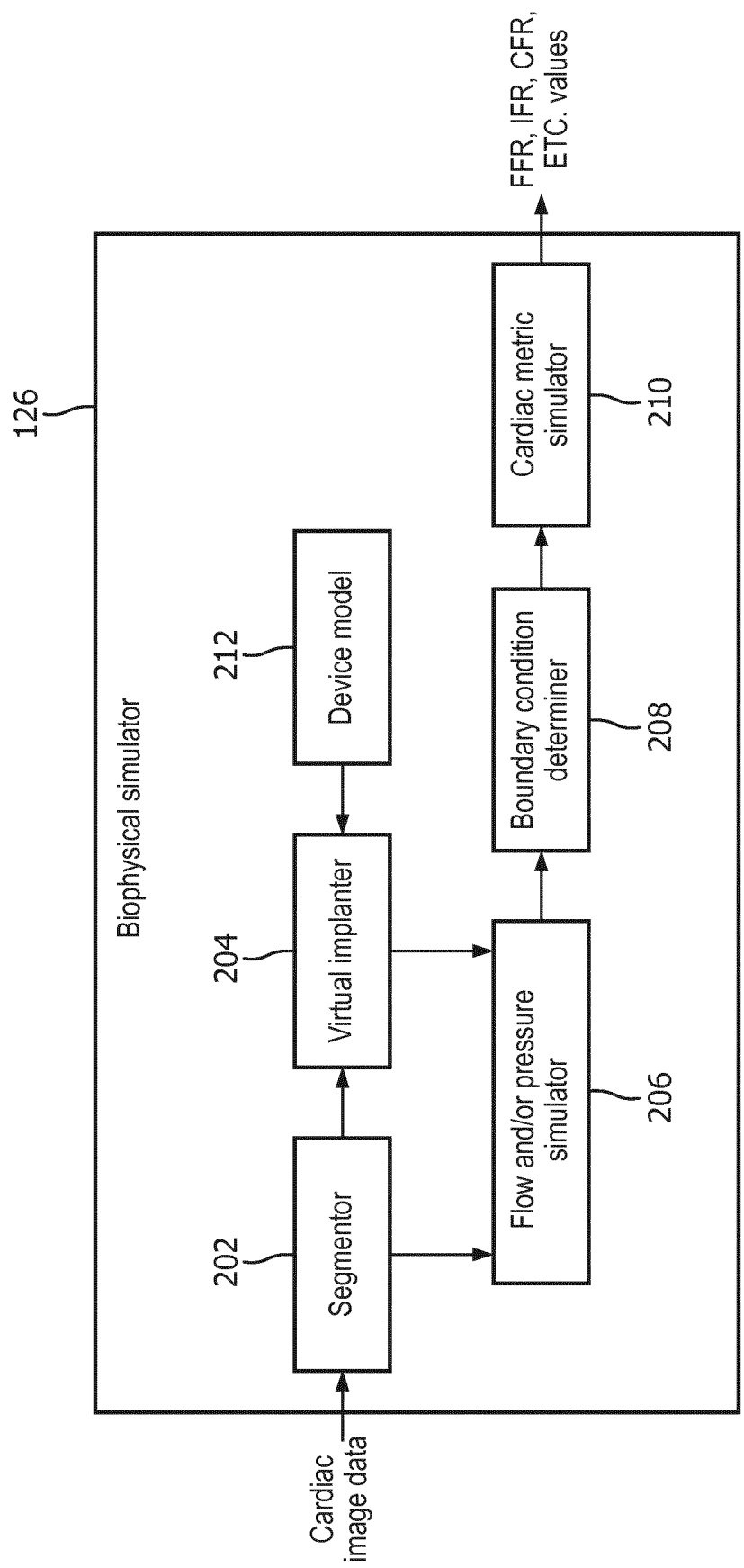
FIG. 2 schematically illustrates an example of the biophysical simulator.

FIG. 2 schematically illustrates an example of the biophysical simulator 126. In this example, the biophysical simulator 126 includes a segmentor 202, a virtual implanter 204, a flow and/or pressure simulator 206, a boundary condition determiner 208, and a cardiac metric simulator 210. The biophysical simulator 126 receives, as input, image data from the imaging system 100, a data repository (e.g., a radiology information system (RIS), a picture and archiving system (PACS), etc.), portable memory, and/or other apparatus.

In a variation, the biophysical simulator 126 is accessed via a web service. In this variation, the image data is transferred (uploaded) from the imaging system 100 and/or other system to the biophysical simulator 126 through the web service. The biophysical simulator 126 remotely processes the image data as described herein. The results are then transferred back (downloaded) to the imaging system 100 and/or other system. Alternatively, or additionally, the results are displayed and/or further analyzed with the web service and/or other service.

The segmentor 202 employs a segmentation algorithm to segment and determine a shape of at least the left ventricle, the aorta, and the coronary tree from the image data. The segmentation can be performed automatically or semi-automatically (e.g., with user assistance). In one instance, the result is a surface model of the vascular anatomy. With one approach, the heart is first localized using a Hough transform, a mesh is initialized by assigning an affine transformation to each anatomical region, and then a deformable adaptation is performed to match the boundaries of the patient's anatomy. An example is discussed in Ecabert et al., "Automatic Model-Based Segmentation of the Heart in CT images," IEEE Transactions on Medical Imaging, Vol. 27, No. 9, September 2008.

Figure 3:
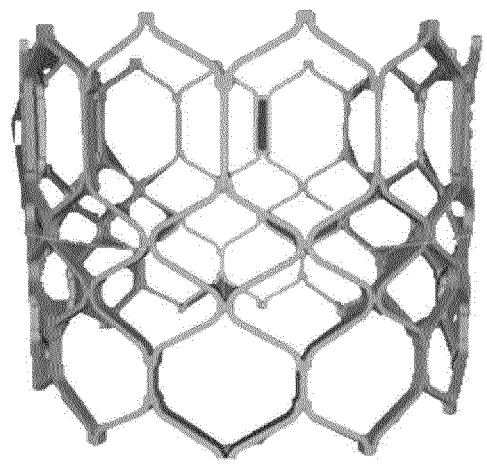
FIG. 3 illustrates an example device model of an aortic valve.
Figure 4:
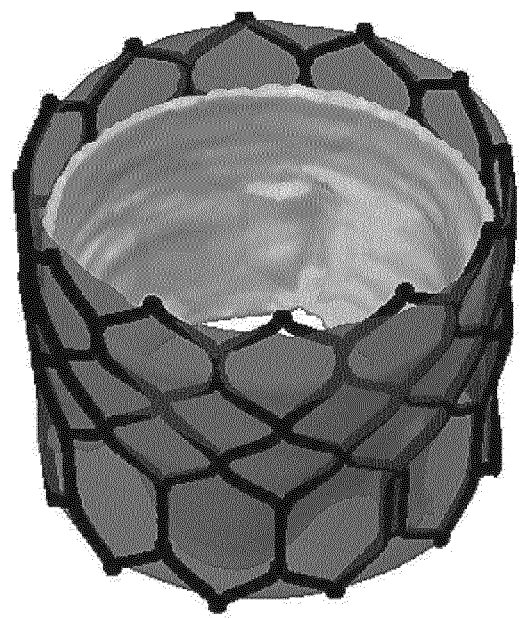
FIG. 4 illustrates an example of the device model virtually implanted.

The virtual implanter 204 virtually implants a digital device model 212 into the segmented image data. The virtual implant can be performed using a rigid and/or elastic adaptation process. For a virtual aortic valve implant, in one instance, the device model 212 is initially smaller than the aortic valve and is suitable positioned at the aortic root. The device model 212 is then grown (increased in size) until it touches the walls. Pixel intensity, an edge detection algorithm, and/or other approach can be used to detect when the virtual implant touches the walls. A biomechanical simulation can be used to facilitate virtual placement. FIG. 3 schematically illustrates an example TAVI model. FIG. 4 schematically illustrates the model virtually implanted and represented by a triangulated mesh about a valve. An example of virtual device implantation is described in application EP17305824.9, filed on Jun. 29, 2017, and entitled "Device and method for predicting an unfolded state of a foldable implant in cardiovascular tissue," which is incorporated herein by reference in its entirety.

The flow and/or pressure simulator 206 simulates a flow and/or pressure distal to the aortic valve from the original segmented image data and the segmented image data with the implant. In one instance, the simulator 206 simulates the flow and/or pressure using a computational fluid dynamics (CFD) simulation, and simulates valve induced flow changes and regurgitation effects. Where an invasive evaluation of the aortic and coronary anatomy is performed as a part of a Cath Lab procedure prior to an actual implantation, flow and/or pressure measures can be taken then and used instead of or in addition to the simulated flow and/or pressure from the original segmented image data. Other invasive measurements in the aorta and/or the ventricle can also be taken.

The boundary condition determiner 208 determines boundary conditions for a cardiac metric simulation. With one approach, a parametric lumped model is employed. The model includes elements indicating inflow and outflow boundary conditions, represented using linear and nonlinear resistance elements reflecting vessel geometry and/or hydraulic effects. The simulated and/or measured flow and/or pressure distal to the aortic valve and into the coronary arteries are used as boundary conditions. The flow in the aorta may be distributed to the coronary ostia according to a computational fluid dynamics calculation or due to their cross-sectional areas relative to the aortic area, or using another approach.

An example of a lumped model is discussed in Nickisch, et al., "Learning Patient-Specific Lumped Models for Interactive Coronary Blood Flow Simulations," in Medical Image Computing and Computer-Assisted Intervention—MICCAI 2015: 18th International Conference, LNCS, Vol. 9350, 2015, vol. 9350, pp. 433-441. An example of deriving boundary conditions is described in EP14174891.3, filed Jun. 30, 2014, and entitled "Enhanced Patient's Specific Modelling For FFR-CT," which is incorporated herein by reference in its entirety. Other approaches are also contemplated herein.

The cardiac metric simulator 210 performs a simulation of the pressure distribution and flow characteristics in the coronaries arteries pre- and post-virtual implantation. In one instance, this includes calculating a coronary state metric such as a fractional flow reserve (FFR), instantaneous wave-free ratio (iFR), a coronary flow reserve (CFR), and/or other metric. A difference between pre- and post-implant metrics predicts an influence of a TAVI on the functional performance of the coronary arteries. The pre- and post-implant metrics and/or the difference there between can be visually displayed.

Although the flow and/or pressure simulator 206 and cardiac metric simulator 210 are shown as separate components in FIG. 2, in another embodiment they are part of a same single simulator, e.g., the flow and/or pressure simulator 206, the cardiac metric simulator 210, and/or another simulator.

Figure 5:
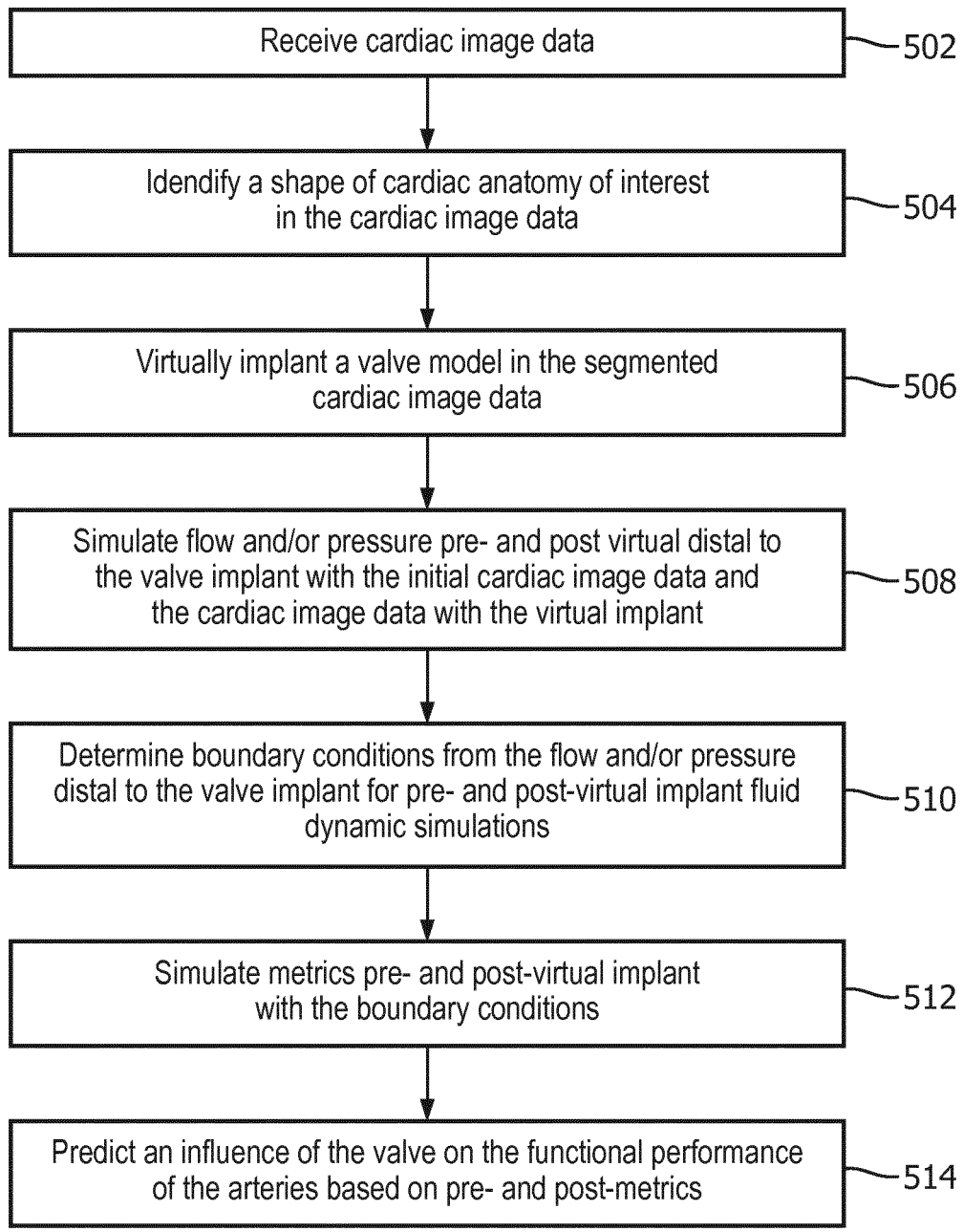
FIG. 5 illustrates an example method in accordance with an embodiment herein.

FIG. 5 illustrates an example method in accordance with an embodiment described herein.

It is to be appreciated that the ordering of the acts is not limiting. As such, other orderings are contemplated herein. In addition, one or more acts may be omitted and/or one or more additional acts may be included.

At 502, cardiac image data is received.

At 504, the cardiac image data is segmented to identify a shape of cardiac anatomy of interest, as described herein.

At 506, a valve device model is virtually implanted in the segmented cardiac image data, as described herein and/or otherwise.

At 508, flow and/or pressure simulations are performed using the initial cardiac image data and the cardiac image data with the virtual implant to determine flow and/or pressure distal to the valve pre- and post-virtual implant, as described herein and/or otherwise.

At 510, boundary conditions for fluid dynamic simulations of the coronary and/or carotid arteries, pre- and post-virtual implant, are determined using the simulated flow and/or pressure distal to the valve, as described herein and/or otherwise.

At 512, coronary and/or carotid state metric simulations, pre- and post-virtual implant, are performed using the boundary conditions, as described herein and/or otherwise.

At 514, a predicted influence of an actual physical valve on the functional performance of the coronary and/or carotid arteries is determined based thereon.

Figure 6:
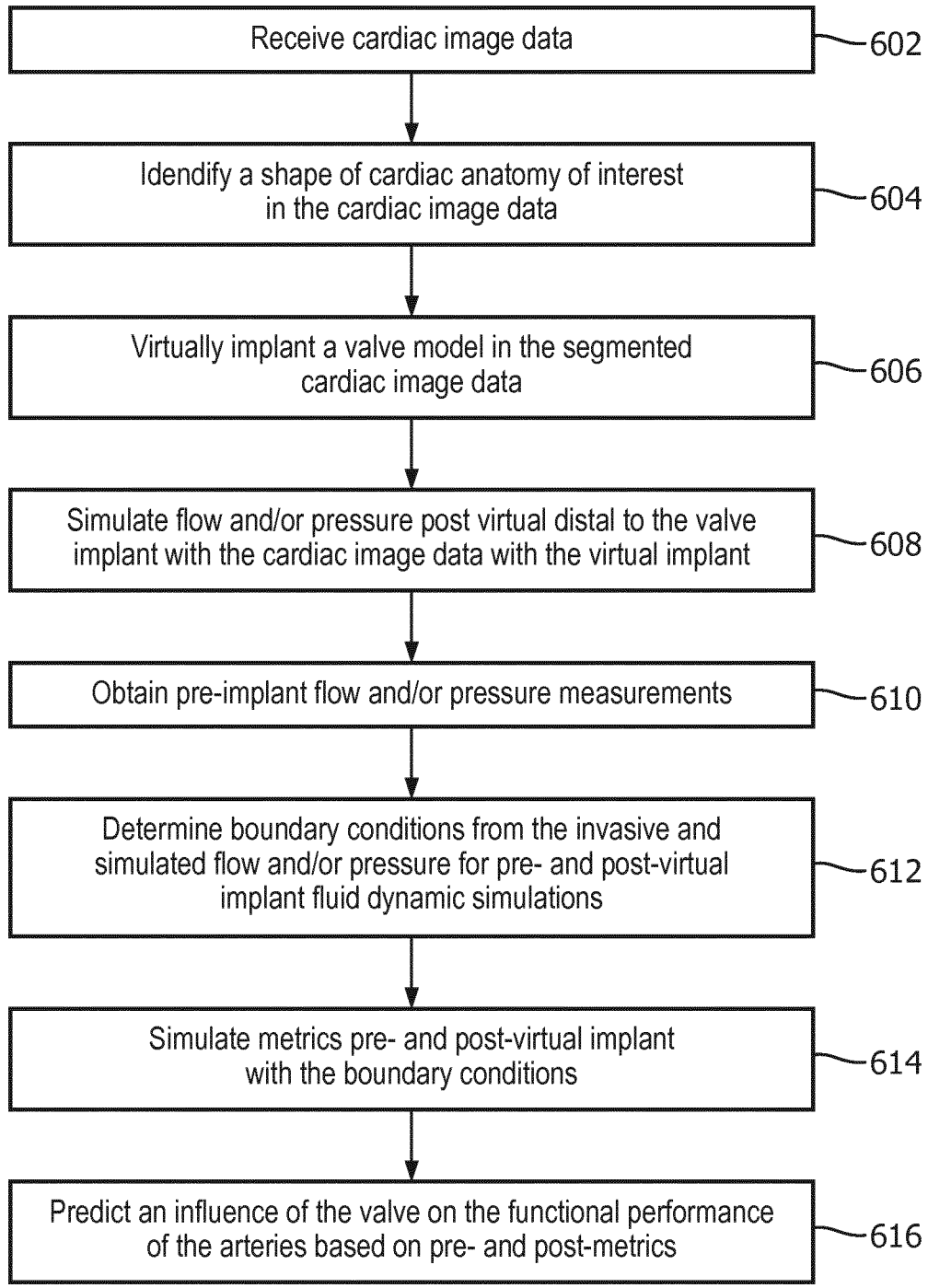
FIG. 6 illustrates another example method in accordance with an embodiment herein.

FIG. 6 illustrates another example method in accordance with an embodiment described herein. Generally, FIG. 6 is a variation to FIG. 5 that uses invasive measurements as pre-implant boundary conditions.

It is to be appreciated that the ordering of the acts is not limiting. As such, other orderings are contemplated herein. In addition, one or more acts may be omitted and/or one or more additional acts may be included.

At 602, cardiac image data is received.

At 604, the cardiac image data is segmented to identify a shape of cardiac anatomy of interest, as described herein.

At 606, a valve device model is virtually implanted in the segmented cardiac image data, as described herein and/or otherwise.

At 608, flow and/or pressure simulations are performed the cardiac image data with the virtual implant to determine flow and/or pressure distal to the valve post-virtual implant, as described herein and/or otherwise.

At 610, pre-implant invasive flow and/or pressure measures are obtained, as described herein and/or otherwise.

At 612, boundary conditions for fluid dynamic simulations of the coronary and/or carotid arteries, pre- and post-virtual implant, are determined respectively using the invasive and simulated flow and/or pressure, as described herein and/or otherwise.

At 614, coronary and/or carotid state metric simulations, pre- and post-virtual implant, are performed using the boundary conditions, as described herein and/or otherwise.

At 616, a predicted influence of an actual physical valve on the functional performance of the coronary and/or carotid arteries is determined based thereon.

Figure 7:
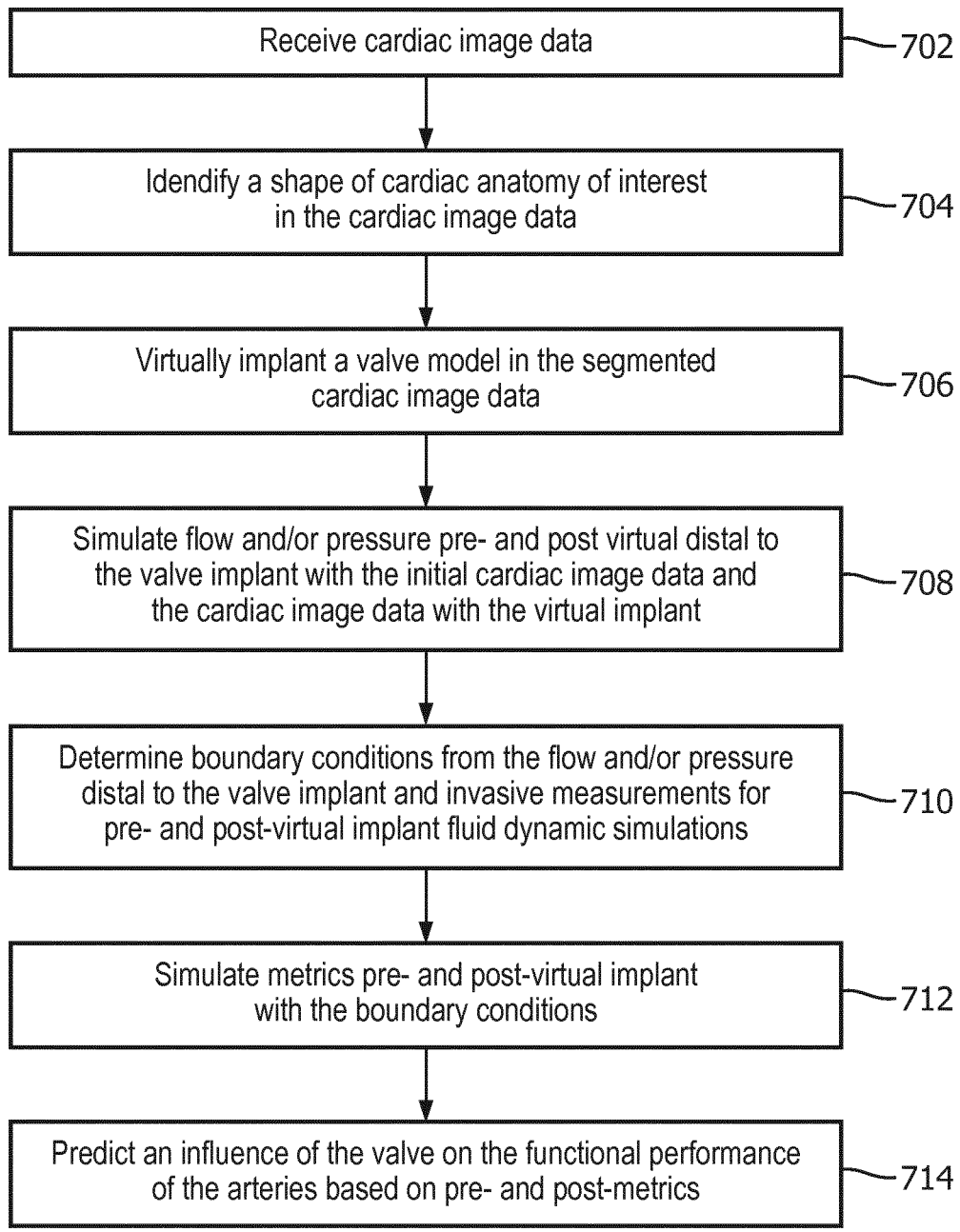
FIG. 7 illustrates another example method in accordance with an embodiment herein.

FIG. 7 illustrates an example method in accordance with an embodiment described herein. Generally, FIG. 7 is a combination of FIGS. 5 and 6, using both simulated and invasive measurements as boundary conditions.

It is to be appreciated that the ordering of the acts is not limiting. As such, other orderings are contemplated herein. In addition, one or more acts may be omitted and/or one or more additional acts may be included.

At 702, cardiac image data is received.

At 704, the cardiac image data is segmented to identify a shape of cardiac anatomy of interest, as described herein.

At 706, a valve device model is virtually implanted in the segmented cardiac image data, as described herein and/or otherwise.

At 708, flow and/or pressure simulations are performed using the initial cardiac image data and the cardiac image data with the virtual implant to determine flow and/or pressure distal to the valve pre- and post-virtual implant, as described herein and/or otherwise.

At 710, boundary conditions for fluid dynamic simulations of the coronary and/or carotid arteries, pre- and post-virtual implant, are determined using the simulated flow and/or pressure distal to the valve and invasive flow and/or pressure measures, as described herein and/or otherwise.

At 712, coronary and/or carotid state metric simulations, pre- and post-virtual implant, are performed using the boundary conditions, as described herein and/or otherwise.

At 714, a predicted influence of an actual physical valve on the functional performance of the coronary and/or carotid arteries is determined based thereon.

The above may be implemented by way of computer readable instructions, encoded or embedded on computer readable storage medium, which, when executed by a computer processor(s), cause the processor(s) to carry out the described acts. Additionally, or alternatively, at least one of the computer readable instructions is carried by a signal, carrier wave or other transitory medium, which is not computer readable storage medium.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system for processing medical images, comprising:
a memory that stores a plurality of instructions;
at least one processor that couples to the memory and is configured to execute the plurality of instructions to:
receive a cardiac image;
receive a model of a cardiac valve device;
segment the cardiac image to determine a shape of cardiac anatomy of interest;
determine boundary conditions based on the segmentation;
simulate a pre-implant arterial blood flow metric and/or a pre-implant pressure metric according to the boundary conditions and the segmentation;
virtually implant the model into the segmented cardiac image;
determine the boundary conditions based on the segmentation with the virtually implanted model;
simulate a post-implant arterial blood flow metric and/or a post-implant pressure metric according to the boundary conditions, the segmentation, and the virtually implanted model; and
predict an effect of implanting the cardiac valve device based on the simulations.

2. The system of claim 1, wherein the at least one processor is configured to determine the boundary conditions based on invasive flow and/or pressure measurements.

3. The system of claim 1, wherein the pre- and post-implant metrics include at least one of a fractional flow reserve, an instantaneous wave-free ratio, and a coronary flow reserve.

4. The system of claim 3, further comprising a display configured to visually present the pre- and post-implant metrics.

5. The system of claim 3, wherein the at least one processor is configured to determine a difference between the pre-implant metric and the post-implant metric.

6. The system of claim 1, wherein the model is a model of a transcatheter aortic valve implantation device.

7. A non-transitory computer readable storage medium for storing executable instructions, which cause a method to be performed for processing medical images, the method comprising:
receiving a cardiac image;
receiving a model of a cardiac valve device implant;
segmenting the cardiac image to determine a shape of cardiac anatomy of interest;
determining boundary conditions based on the segmentation;
simulating a pre-implant arterial blood flow metric and/or a pre-implant pressure metric according to the boundary conditions and the segmentation;
virtually implanting the model into the segmented cardiac image;
determining the boundary conditions based on the segmentation with the virtual implanted model;
simulating a post-implant arterial blood flow metric and/or a post-implant pressure metric according to the boundary conditions, the segmentation, and the virtually implanted model; and
predicting an effect of implanting the cardiac valve device implant based on the simulations.

8. The non-transitory computer readable storage medium of claim 7, wherein the at least one processor is configured to determine boundary conditions based invasive flow and/or pressure measurements.

9. The non-transitory computer readable storage medium of claim 7, wherein the at least one processor is configured to determine a difference between the pre-implant metric and the post-implant metric.

10. The non-transitory computer readable storage medium of claim 9, wherein the processor is configured to visually present the pre-implant metric and the post-implant metric.

11. A computer-implemented method for processing medical images, comprising:
receiving a cardiac image;
receiving a model of a cardiac valve device implant;
segmenting the cardiac image to determine a shape of cardiac anatomy of interest;
determining boundary conditions based on the segmentation;
simulating a pre-implant arterial blood flow metric and/or a pre-implant pressure metric according to the boundary conditions and the segmentation;
virtually implanting the model into the segmented cardiac image;
determining the boundary conditions based on the segmentation with the virtual implanted model;
simulating a post-implant arterial blood flow metric and/or a post-implant pressure metric according to the boundary conditions, the segmentation, and the virtually implanted model; and
predicting an effect of implanting the cardiac valve device implant based on the simulations.

12. The method of claim 11, further comprising:
computing a difference between the pre-implant metric and the post-implant metric.

13. The method of claim 11, further comprising:
visually displaying at least one of the pre-implant metric and the post-implant metric, and the difference therebetween.

14. The method of claim 11, further comprising determining the boundary conditions based on invasive flow and/or pressure measurements.

15. The method of claim 11, wherein the pre-implant metric and the post-implant metric include at least one of a fractional flow reserve, an instantaneous wave-free ratio, and a coronary flow reserve.

* * * * *